(12) United States Patent
Olson et al.

(10) Patent No.: US 10,712,409 B2
(45) Date of Patent: Jul. 14, 2020

(54) SAMPLING SYSTEM AND METHOD

(71) Applicant: Spectro Scientific, Inc., Chelmsford, MA (US)

(72) Inventors: Eric John Olson, Philipston, MA (US); Peter Gregory Loges, Harvard, MA (US); David Anthony Malaguti, Stoneham, MA (US)

(73) Assignee: Spectro Scientific, Inc., Chelmsford, MA (US)

( * ) Notice: Subject to any disclaimer, the term of this patent is extended or adjusted under 35 U.S.C. 154(b) by 0 days.

(21) Appl. No.: 16/016,982

(22) Filed: Jun. 25, 2018

(65) Prior Publication Data

US 2018/0372597 A1 Dec. 27, 2018

Related U.S. Application Data

(60) Provisional application No. 62/525,390, filed on Jun. 27, 2017.

(51) Int. Cl.
*G01R 33/30* (2006.01)
*G01N 1/36* (2006.01)
*G01N 33/26* (2006.01)

(52) U.S. Cl.
CPC ............... *G01R 33/30* (2013.01); *G01N 1/36* (2013.01); *G01N 33/26* (2013.01)

(58) Field of Classification Search
CPC ................................ G01N 33/26; G01R 33/30
See application file for complete search history.

(56) References Cited

U.S. PATENT DOCUMENTS

| | | | |
|---|---|---|---|
| 7,141,033 B2 * | 11/2006 | Kanjilal | A61B 10/0038 604/1 |
| 7,984,661 B2 | 7/2011 | Wurzbach | |
| 8,549,930 B2 | 10/2013 | Wurzbach et al. | |
| 2008/0127443 A1 * | 6/2008 | Blanchard | B44D 3/126 15/257.06 |
| 2018/0231497 A1 | 8/2018 | Glaberson et al. | |

\* cited by examiner

*Primary Examiner* — Justin N Olamit
(74) *Attorney, Agent, or Firm* — Iandiorio Teska & Coleman, LLP

(57) ABSTRACT

A method of and system for obtaining a consistent volume of a viscous material includes inserting a sample holder portion of a collection device into a body of the viscous material and filling an open, concave sample receptacle of the sample holder portion with the viscous material. A scrapper is used to remove excess viscous material above the open, concave receptacle. The collection device and the viscous material loaded therein are inserted into a sample vial. Then, the sample vial with the collection device therein is inserted into the port of an analyzer.

3 Claims, 6 Drawing Sheets

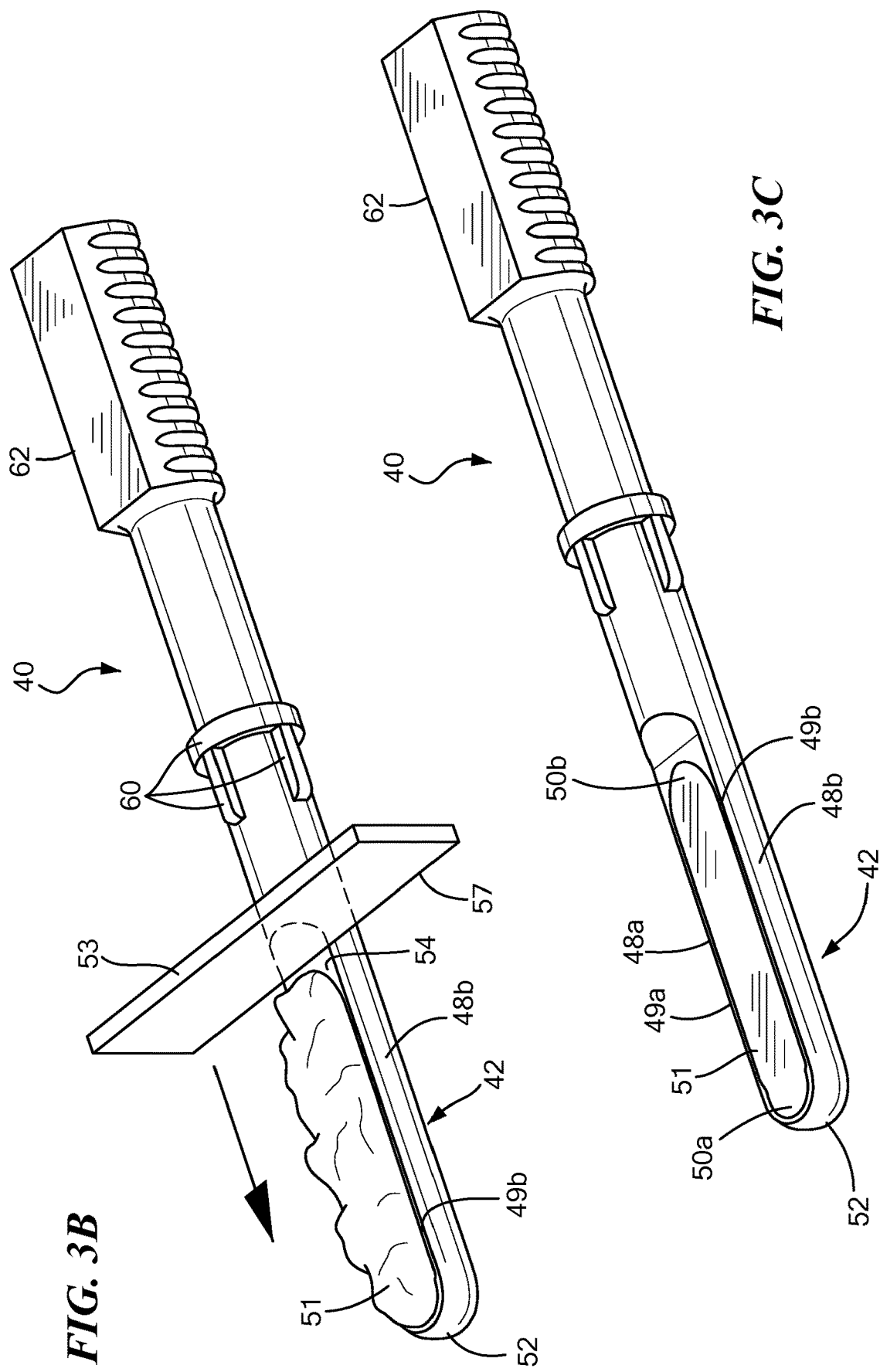

SAMPLING SYSTEM AND METHOD

RELATED APPLICATIONS

This application claims benefit of and priority to U.S. Provisional Application Ser. No. 62/525,390 filed Jun. 27, 2017, under 35 U.S.C. §§ 119, 120, 363, 365, and 37 C.F.R. § 1.55 and § 1.78, which is incorporated herein by this reference.

FIELD OF THE INVENTION

This subject invention relates to sampling systems and methods for viscous samples such as grease.

BACKGROUND OF THE INVENTION

A magnetometer can be used to measure the ferrous material present in an oil sample. See U.S. patent application Ser. No. 15/434,293 by the applicant hereof and incorporated herein by this reference. The oil may be sumped from a machine and delivered to a sample vial which is then inserted into the magnetometer.

A magnetometer can also be used to measure the ferrous material present in more viscous samples such as grease. But, loading grease into a sample vial can be messy and difficult. It is also important to ensure the grease does not contaminate the magnetometer. At the same time, the volume of grease must be consistent. Any air pockets will result in erroneous readings.

In the prior art, spatulas and the like were used to collect grease samples. See ASTM Standard D 7718 incorporated herein by this reference. U.S. Pat. Nos. 7,984,661 and 8,549,930, both incorporated herein by this reference, disclose a grease sampling kit. But, the cost of this kit can be expensive especially for a disposable product.

BRIEF SUMMARY OF THE INVENTION

Featured, in some embodiments, is an inexpensive, disposable, easy to use collection device that ensures a constant volume of viscous material such as grease is presented to an analyzer such as a magnetometer without any air pockets.

Featured is a method of obtaining a consistent volume of a viscous material. A sample holder portion of a collection device is inserted into a body of the viscous material and an open, concave sample receptacle of the sample holder portion is filled with the viscous material. A scrapper is used to remove excess viscous material above the open, concave receptacle. The collection device and the viscous material loaded therein is inserted into a sample vial and the sample vial with the collection device therein is inserted into the port of an analyzer.

In some embodiments the open, concave sample receptacle includes a floor and sidewalls extending upwards from the floor. The open, concave sample receptacle may include beveled ramps at opposing ends of the concave floor. The sample holder portion may include a rounded tip. The sample holder portion may include a flat surface adjacent the open, concave receptacle. The collection device may include a handle extending from the sample holder portion and the handle may include one or more friction fit features and/or one or more gripping features. The handle may include a flat top surface. The handle may be hollow.

Preferably, the collection device is molded of a translucent or transparent plastic material. The sample vial may include a flared open end. Preferably, the sample vial includes a sample chamber with an inter diameter corresponding to the outer diameter of the sample holder portion of the collection device. The sample vial may further include a larger inner diameter section above the sample chamber which corresponds to the friction fit features of the collection device.

Also featured is a viscous material sampling system comprising a collection device including a sample holder portion with an open, concave sample receptacle for a sample, and a handle extending from the sample holder portion. A vial is provided for receiving the collection device therein and for delivering the sample to an analyzer.

Also featured is a viscous material collection device. A sample holder portion includes an open, concave sample receptacle for the viscous material. The sample receptacle includes a concave floor and sidewalls extending upwards from the concave floor. There is a beveled ramp at each end of the concave floor. The device further includes a handle extending from the sample holder portion and a flat surface between the sample holder portion and the handle.

In one embodiment, there is a centerline extending through the handle and sample holder portion and the sidewalls extending up from the concave floor extend above the centerline. Preferably, the flat surface lies in the same plane as the top edges of the sidewalls. The sidewalls may have outer convex or cylindrical surfaces, inner concave lower surfaces, and inner straight upper surfaces.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIGS. 3A-C are schematic three dimensional views showing an example of a collection device in accordance with the invention;

DETAILED DESCRIPTION OF THE INVENTION

Figure 1:
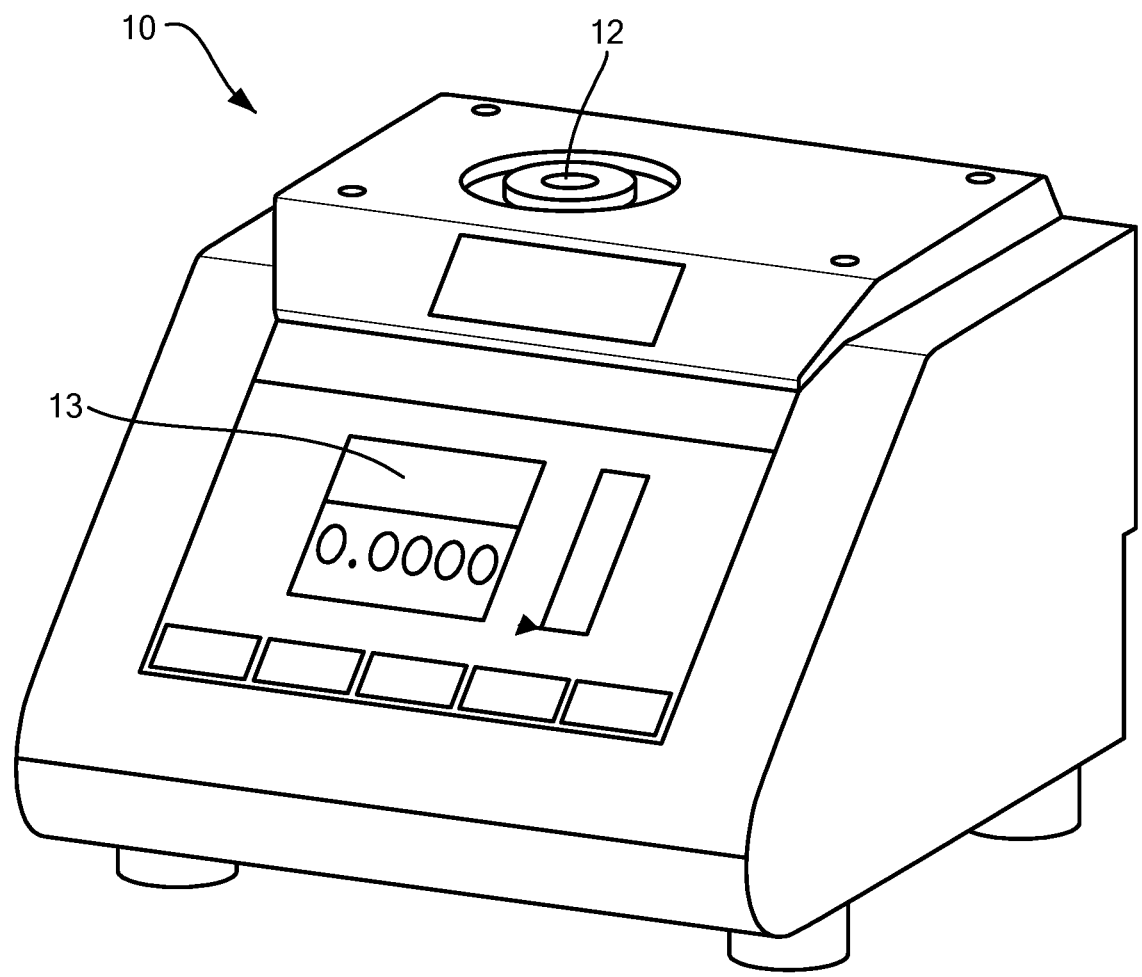
FIG. 1 is schematic view showing an example of a magnetometer.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 2:
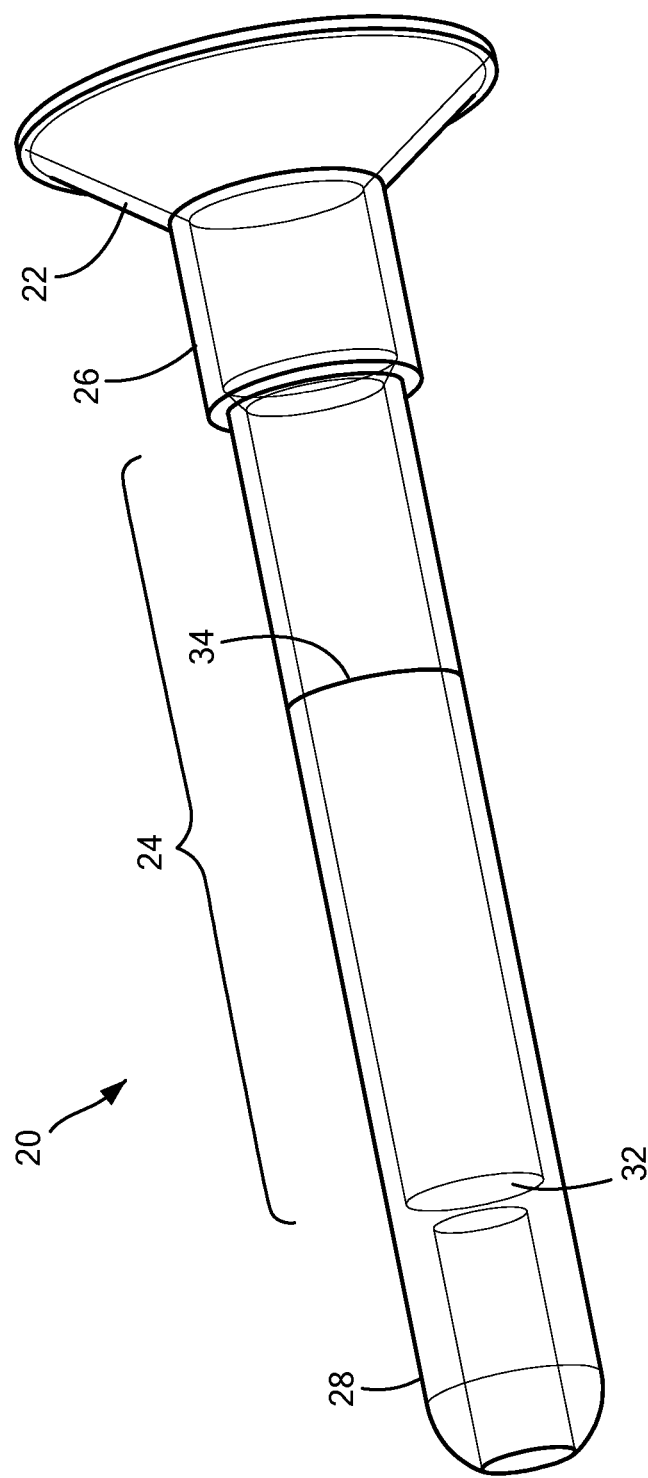
FIG. 2 is a schematic three dimensional view showing an example of a sample vial used in conjunction with the magnetometer of FIG. 1.

FIG. 1 shows a magnetometer 10 with a top port 12 for receiving a sample vial 20, FIG. 2. Magnetometer 10 preferably detects and measures ferrous wear particles in samples taken from engines, gear boxes, and the like. A report may be displayed on screen 13. In this specific example, sample vial 20 includes flared open end 22, sample chamber 24, intermediate section 26, and distal rounded end section 28 (which may be hollow). An oil sample can be loaded into sample chamber 24 via the flared open end 22 and resides between floor 32 of sample chamber 24 and fill line 34. Sample chamber 24 may have an outer diameter of 0.425", an inner diameter of 0.303" and intermediate section 26 may have an outer diameter of 0.500" and an inner diameter of 0.380". The lengths of sections 28 and 24 are selected such that the sample in the vial between floor 32 and fill line 34 is coincidental with sensitive region of the magnetometer coil when the device is placed within the magnetometer and tip 28 is resting against the bottom of chamber 12 or a stop within the chamber.

It is not as easy, however, to load the sample chamber of the vial with a more viscous material such as grease. The process may be messy, the volume of the grease inconsistent, and/or air pockets may be present leading to erroneous measurements. For example, if the volume of a grease sample with 1000 PPM ferrous content is reduced by half, the magnetometer may erroneously report a ferrous content of 500 PPM.

Figure 3A:
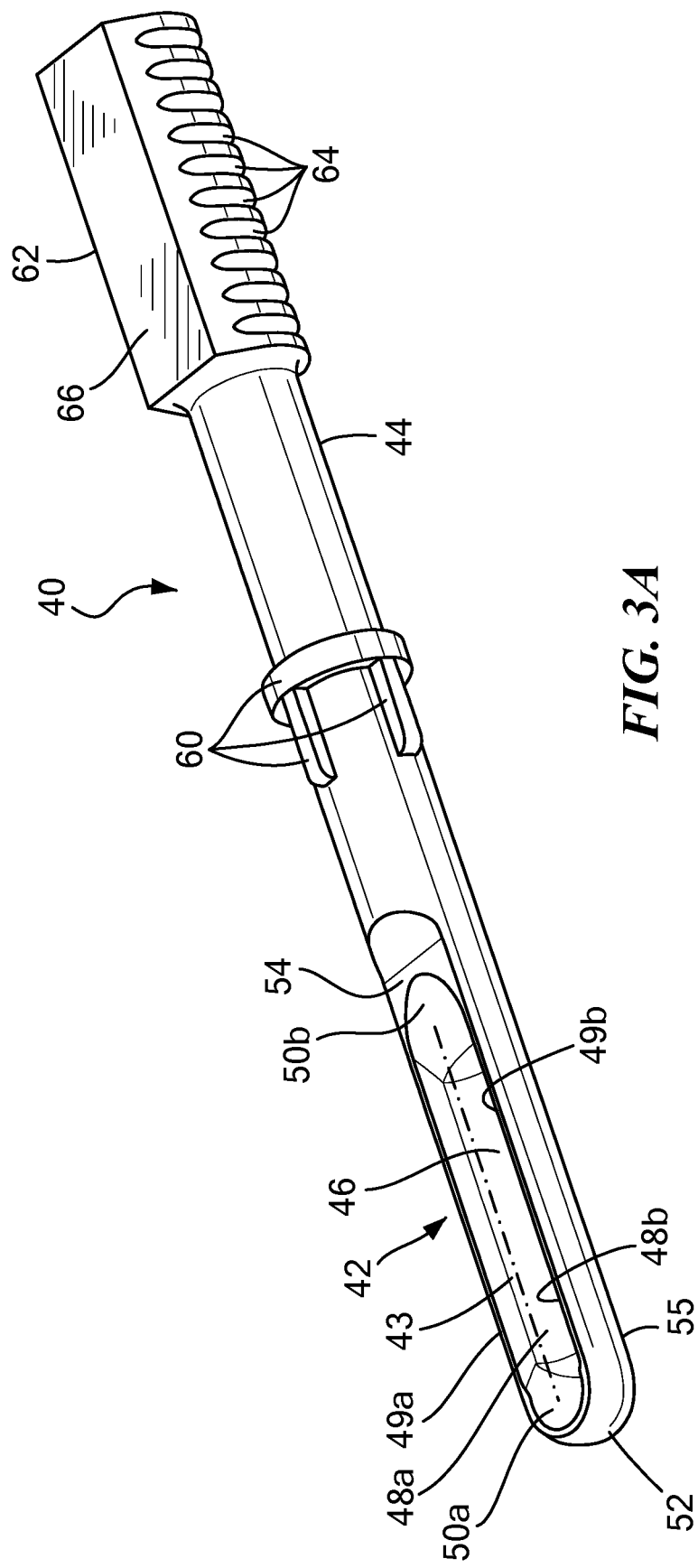

Featured in one particular embodiment is viscous material collection device 40, FIG. 3A. Collection device 40 includes sample holder portion 42 and handle 44 extending therefrom. Preferably, sample holder portion 42 includes an open, concave boat-like sample receptacle with a concave floor 46 and sidewalls 48a, 48b extending vertically upwards therefrom. The outside of the sidewalls may be curved. The inside of the sidewalls may be concave up to the center line level 43 and then the inside of the sidewalls are preferably straight. Ramps 50a, 50b, (e.g., beveled at 45°) help to ensure no air pockets reside in the grease filling the boat-like sample holder portion 42 receptacle. Tip portion 52 of the grease tub device may be rounded as shown. Flat surface 54 adjacent the receptacle provides a surface for a scrapper to be initially placed to begin scrapping grease or another viscous sample above the top flat edges 49a, 49b of the side walls 48a, 48b. A tongue depressor or blade may be used for this procedure.

Figure 4:
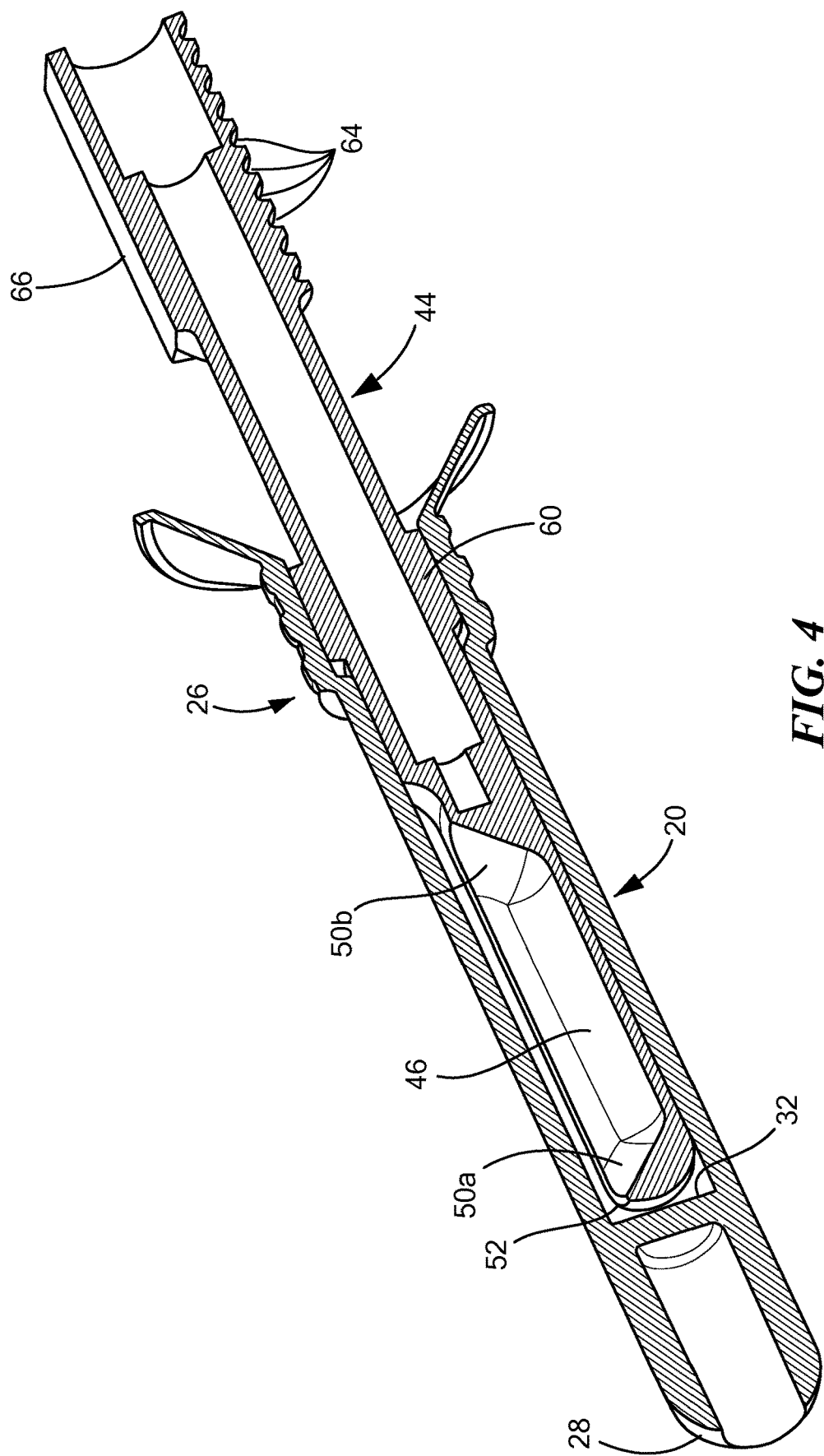
FIG. 4 is a schematic cross-sectional view showing the collection device of FIG. 3 inserted into the sample vial of FIG. 2.

Handle 44 may include one or more friction fit features 60 corresponding in diameter to the inside diameter of section 26, FIG. 4 of the sample vial. Enlarged end 62 of the handle may include one or more gripping features 64 (e.g., indentations or scalloped portions) and flat top surface 66 for the users thumb and/or for notes or labels identifying the grease sample. Handle section 44 may be hollow as shown in FIG. 4 to accept a longer rod or other extender tool for sampling. In other example, the extender tool end surrounds and secures to the outside of enlarged handle end 62.

Preferably, the plastic material used for the collection device is translucent or even transparent so any air pockets in the grease residing in the boat or tub of the sample holder portion receptacle can be readily identified by holding the collection device filled with grease up to a light. In one example, a clarified polypropylene material is used. Preferably, the top edges 49a, 49b of sidewalls 48a, 48b of the receptacle rise up above the center line 43 of the round stock used to form the sample holder portion. This helps ensure the collection device fits tightly inside the sample vial 20, FIG. 4 and movement of the collection device relative to the sample vial is minimized. Also, flat 54 lies in the same plane as the top two edges of 49a, 49b of side walls 48a, 48b so scraper 53 bottom edge 57 proceeds smoothly from flat 54 along the top edges 49a, 49b of side walls 48a, 48b.

Figure 5:
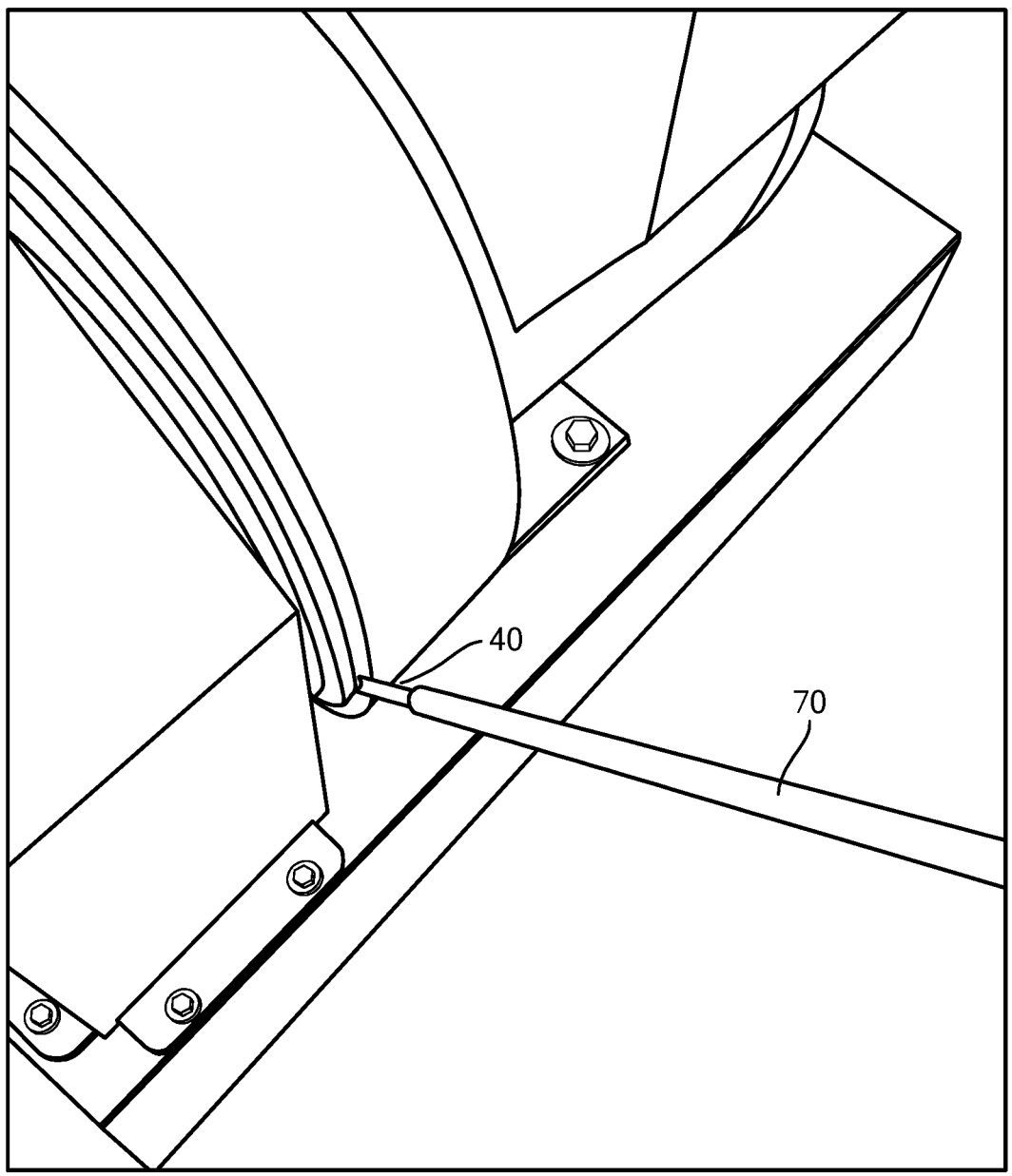
FIG. 5 is a schematic view showing how an extender can be coupled to the handle of the collection device of FIG. 3.

In use, grease or another viscous material to be analyzed is collected from a machine or device and placed in a cup. Sample holder portion 42 of the collection device is then driven into the grease and a sample scooped therefrom. In other examples, the sample holder portion 42 is driven into a grease sample present in or on a machine (using, for example, an extender tool 70, FIG. 5 which receives the handle portion therein or which is inserted into the hollow handle portion). The grease 51, FIG. 3B or other viscous material is thus loaded into the concave boat or tube receptacle of the sample holder portion 42.

Then, a scrapper 53 is placed on flat 54, FIG. 3B and urged towards end 52 so now grease fills sample holder boat receptacle up to the level of the top edges of sidewalls 48a, 48b and between the top edges of ramps 50a, 50b as shown in FIG. 3C. Next, the collection device is placed into vial 20, FIG. 4 until end 52 rests on floor 32 as shown in FIG. 4. Finally, this combination is placed into port 12, FIG. 1 of magnetometer 10 (or into some other analyzer).

The result is a new sampling tool and a method of keeping the test equipment clean. The grease boat or tub of the open concave sample holder portion receptacle has a cross section optimized for a highly viscous sample collection without air voids. The extended collection area assists in guaranteeing a consistent sample volume placed into the magnetometer. The sectioned area of the open concave sample holder portion receptacle allows for easy packing of a highly viscous sample. The handle, typically a cylindrical tube, can be attached to an extended arm, holder, or tool to reach into a compartment to collect a sample. The end is preferably flared or tapered to mate to the extender arm and/or tool. This allows for the operator to have different length attachments to collect samples in remote locations. Once a sample is collected, the cross-sectioned surface acts as a reference surface for a screed to be used to remove any excess sample material. The collection device is designed to be of a matching outer diameter and tapered to fit snugly into a mating sample vial. The action of inserting the collection device into the sample vial helps clear any excess material from the rounded bottom surface 55, FIG. 3A of the collection device to ensure a consistent volume of the sample reaches the bottom of the vial and is later presented to the analyzer.

In one version, holder 40 is 3.89 inches long. The sample holder portion is 1.36 inches long, 0.230 inches wide, and 0.22 inches deep. The outer diameter of holder 40 handle 44 may be 0.290 inches and the inner diameter of vial 20 may be 0.303 inches.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. A viscous material collection device comprising:
    a sample holder portion including an open, concave sample receptacle for the viscous material, the sample receptacle including a distal tip, a concave floor, and sidewalls extending upwards from the concave floor;
    a first beveled ramp at the distal tip of the sample receptacle;
    a second beveled ramp opposite the first beveled ramp;
    a handle extending from the sample holder portion;
    a flat surface proximate the second beveled ramp between the sample holder portion and the handle;
    a centerline extending through the handle and sample holder portion;
    the sidewalls extending upwards from the concave floor extend above said centerline; and
    the sidewalls have top edges and the flat surface lies in the same plane as the top edges of the sidewalls.

2. The device of claim 1 in which the sidewalls have outer convex surfaces.

3. The device of claim 1 in which the sidewalls have inner concave lower surfaces and inner straight upper surfaces.

* * * * *